United States Patent [19]
Plouhar et al.

[11] Patent Number: 5,788,625
[45] Date of Patent: Aug. 4, 1998

[54] METHOD OF MAKING RECONSTRUCTIVE SIS STRUCTURE FOR CARTILAGINOUS ELEMENTS IN SITU

[75] Inventors: Pamela L. Plouhar, South Bend; Michael D. Dunn, Winona Lake; Jerry L. Lower, Bourbon; Thomas C. May, Winona Lake, all of Ind.

[73] Assignee: DePuy Orthopaedics, Inc., Warsaw, Ind.

[21] Appl. No.: 628,773

[22] Filed: Apr. 5, 1996

[51] Int. Cl.⁶ .................................................. A61F 2/04
[52] U.S. Cl. ............................ 600/36; 600/37; 623/11; 623/13; 623/901
[58] Field of Search ........................ 623/11, 13, 901; 600/36, 37

[56] References Cited

U.S. PATENT DOCUMENTS

| | | | |
|---|---|---|---|
| 2,127,903 | 8/1938 | Bowen | 128/334 |
| 3,562,820 | 2/1971 | Braun | 3/1 |
| 4,585,458 | 4/1986 | Kurland | 623/13 |
| 4,773,418 | 9/1988 | Hettich | 600/36 |
| 4,902,508 | 2/1990 | Badylak et al. | 424/551 |
| 4,956,178 | 9/1990 | Badylak et al. | 424/551 |
| 5,275,826 | 1/1994 | Badylak et al. | 424/551 |
| 5,281,422 | 1/1994 | Badylak et al. | 424/551 |
| 5,352,463 | 10/1994 | Badylak et al. | 424/551 |
| 5,372,821 | 12/1994 | Badylak et al. | 424/551 |
| 5,503,638 | 4/1996 | Cooper et al. | 623/11 |

FOREIGN PATENT DOCUMENTS

WO 95/06439  3/1995  WIPO .

OTHER PUBLICATIONS

"Comparison of Bovine Collagen Xenografts to Autografts in the Rabbit", J.C. Tauro, et al., *Clinical Orthopaedics and Related Research*, No. 266, May, 1991, pp. 271–284.

"Development of a Reconstituted Collagen Tendon Prosthesis", Jack D. Goldstein, et al., *The Journal of Bone and Joint Surgery, Incorporated*, vol. 71-A, No. 8, Sep. 1989, pp. 1183–1191.

"Replacement of Dog's Aorta by Autologous Intestinal Muscle in the Infected Retroperitoneum", R. Broll, et al., *Eurp. Surg. Res.*, 18:390–396 (1986).

"Aortic Replacement with Multi-Layer Submucosa Prostheses Made From Heterologous Small Intestine", G. Rotthoff, et al., presented at 8th Congress of the International Society of Cardiovascular Surgery, Vienna, Sep. 7–9, 1967.

(List continued on next page.)

*Primary Examiner*—Paul B. Prebilic
*Attorney, Agent, or Firm*—Barnes & Thornburg

[57] ABSTRACT

A reconstructive structure for a cartilaginous element having a plurality of superimposed layers of a small intestine submucosa compressed and secured together and shaped to provide the multi-layered reconstructive element of the anatomical shape of the cartilaginous element to be constructed. The method of forming the reconstructive structure includes superimposing the planar layers of the small intestine compressing, securing and cutting to the desired shape. The superimposing is performed so as to maintain the layers substantially planar prior to compressing and securing. The method of reconstructing a cartilaginous element includes removing at least a portion, if not substantially all of the cartilaginous element, but leaving a seed portion, sculpturing the reconstructive structure to the anatomical shape of the cartilaginous element to be reconstructed; positioning the receptive element adjacent to the seed portion and securing it thereto. To reconstruct a joint having two bones separated by a cartilaginous material, the method includes removing any remaining portions of the cartilaginous material down to a bleeding bone site and positioning and securing the reconstructive element to the bleeding bone site. A barrier layer may be provided between the bleeding bone site and the reconstruction element. Also, a defect site without a bleeding bone site may be created and used with a reconstructive element.

11 Claims, 4 Drawing Sheets

OTHER PUBLICATIONS

"Replacement of the Abdominal Aorta by an Ileum Muscle Tube in an Animal Experiment", J. Huth, et al., (translation), *Thoraxchir. Vask, Chir.*, 15(4): 401–407, Aug. 1967.

"Long Term Observations and Histological Studies on Vessel and Heart Wall Grafts From Small Intestine", R. Haring, et al., (translation) *Langenbecks Arch. Klin. Chir.*, 1965, 313:664–8.

"Replacement of the Abdominal Aorta with a Small–Intestine Muscle Tube in an Animal Experiment", J. Huth, (translation) *Zentralbl Chir.*, 92 (26/2): 1817–19 (1967).

"Reconstruction of the Arterial Flow Path by Autologous Intestinal Muscle Grafts in the Dog", H.P. Bruch, et al., (translation) *Folia Angiologica*, vol. 29 (3–5/1981) pp. 65–68.

"Replacement of the Aorta by Multilayered Submucosa Prostheses of Heterologous Ileum", G. Rotthoff, et al., (translation) *Bulletin de la Societe International de Chirurgie*, No. 2, 1969, 256–259.

"Experimental Replacement of Superior Vena Cava", Fraser, et al., *Arch. Surg.*, vol. 96, Mar. 1968, pp. 378–385.

"Evaluation of Canine Intestinal Submucosa as a Vascular Substitute", Lawler, et al., *The American Journal of Surgery*, vol. 122, Oct. 1971, pp. 517–519.

"Glutaraldehyde Treated Cat Small Bowel as an Arterial Graft", Dagan, et al., *Vascular Surgery*, Jul./Aug. 1983, pp. 199–206.

"A Study of Inverted Intestinal Graft in the Major Veins", Matsumoto, et al., presented at the *Eleventh Annual Meeting of the American College of Angiology*, New York, Jun. 1966, pp. 842–850.

"The Fate of the Inverted Segment of Small Bowel Used for the Replacement of Major Veins", Matsumoto, et al., *Surgery*, vol. 60, No. 3, Sep. 1966, pp. 739–743.

"Experimental Study of Vascular Graft II. Replacement of Inferior Vena Caca and Abdominal Aorta with the Autogenous Segment of Small Intestinal Submucosa", Egusa, S., *Acta. Med Okayama*, 22, 153–165 (1968).

"The Instruments of Surgery", by Francis Mitchell–Heggs and H. Guy Radcliffe Drew; *William Heinemann Medical Books, Ltd.*, London, 1963.

"Use of Freely Transplanted Ileum to Replace Plastic in Cardio–Vascular Surgery", Rotthoff, et al., *Langenbecks Archiv. Klin. Chir.*, 1964, 308, pp. 816–820.

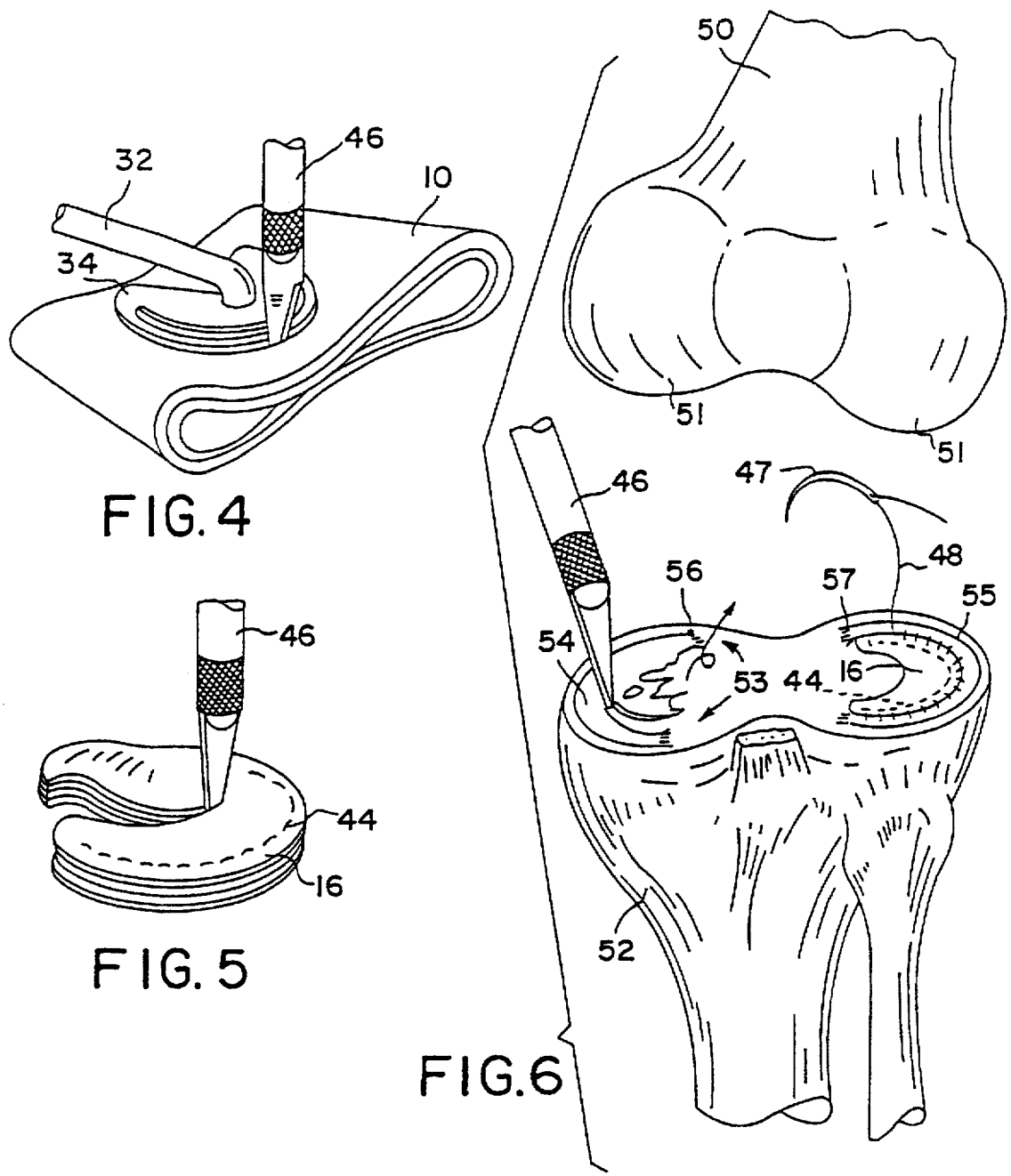

5,788,625

1

METHOD OF MAKING RECONSTRUCTIVE SIS STRUCTURE FOR CARTILAGINOUS ELEMENTS IN SITU

BACKGROUND AND SUMMARY OF THE INVENTION

The present invention relates generally to cartilaginous reconstruction and more specifically to a method of forming a reconstructive structure for cartilage elements, reconstructing a cartilage element in situ using the reconstructive structure and reconstructing a joint having two bones separated by cartilage material.

Researchers in the surgical arts have been working for many years to develop new techniques and materials for use as grafts to replace or repair damaged or diseased tissue structures, particularly bones, cartilaginous tissue and connective tissues, such as ligaments and tendons, and to hasten fracture healing. It is very common today, for instance, for an orthopaedic surgeon to harvest a patellar tendon of autogenous or homologous origin for use as a replacement for a torn cruciate ligament. The surgical methods for such techniques are well known. Further, it has become common for surgeons to use implantable prostheses formed from plastic, metal and/or ceramic material for reconstruction or replacement of physiological structures.

It has been reported that compositions comprising the submucosa of the intestine of warm-blooded vertebrates can be used as tissue graft materials in sheet form. See U.S. Pat. No. 4,902,508. The preferred sheet compositions described and claimed in that patent are characterized by excellent mechanical properties, including high compliance, a high burst pressure point, and an effective porosity index which allowed such compositions to be used beneficially for vascular graft constructs.

The graft materials disclosed in that patent are also useful in tendon and ligament replacement applications as described in U.S. Pat. No. 5,281,422. When used in such applications the graft constructs appear to serve as a matrix for the growth of the tissues replaced by the graft constructs. When used in cruciate ligament replacement experiments not only does the portion of the graft traversing the joint become vascularized and actually grow to look and function like the original ligament, but the portion of the graft in the femoral and tibial bone tunnels rapidly incorporates into and promotes development of the cortical and cancellous bone in those tunnels. It was believed that such properties derived from the sheet structures of the intestinal tissue derived graft constructs. U.S. Pat. No. 5,281,422 also describes in FIGS. 8 and 9 doubling the graft back over itself, one layer on top of the other or rolling it concentrically, one layer on top of the other.

An advantage of the intestinal submucosa graft formed for surgical repair is its resistance to infection. The intestinal graft material, fully described in the aforesaid patents, have high infection resistance, long shelf life and storage characteristics. It has been found that xenogeneic intestinal submucosa is compatible with hosts following implantation as vascular grafts, ligaments and tendons and is not recognized by the hosts'immune system as "foreign" and therefore is not rejected.

As described in U.S. Pat. No. 5,275,826, fluidized intestinal submucosa can be injected into host tissues in need of repair, for example, bone and soft tissue such as muscle and connective tissues. Also described is the surgical reconstruction of a collagenous meniscus at the interface of articulating bones. In such reconstruction a sheet of a first tissue graft composition, preferably itself comprising intestinal submucosa of a warm-blooded vertebrate, is formed into a sealed pouch and filled with the fluidized tissue graft composition of intestinal submucosa.

An object of the present invention is to use the properties of intestinal submucosa for reconstruction of cartilaginous elements.

Another object of the present invention is to provide a method of forming a reconstructive structure for cartilaginous elements.

An even further object of the invention is to describe the method of reconstructing cartilaginous element in situ using an intestinal submucosa structure.

A still further object of the present invention is to provide a method for reconstructing a joint having two bones separated by cartilaginous material. These and other objects are achieved by a reconstructive structure or construct including a plurality of superimposed layers of small intestine submucosa compressed and secured together and shaped to provide a solid multi-layer reconstructive element of the anatomical shape of the cartilaginous element to be reconstructed. The reconstructed structure is formed by superimposing a plurality of sheets of small intestinal submucosa. Superimposed layers are compressed and secured together. The compressed and secured structure is cut and sculptured into the anatomical shape of the cartilaginous element as a solid multi-layered reconstructive structure.

The superimposed layers may be formed by wrapping a continuous piece of small intestinal submucosa about a pair of spaced mandrels. Preferably, the mandrels are positioned to diverge at an acute angle from an apex. This allows the concave edge of the small intestine submucosa to be closer to the apex than the concave edge and therefore compensate for the varying edge length of the small intestine submucosa. This results in a substantially planar structure of the multi-layers. Alternatively, small intestine submucosa is cut into sheets and the sheets are superimposed or stacked. The angular orientation of the sheets in parallel plane may be varied.

A clamp or other tool or hydraulic press may be used to compress the superimposed layers together and hold them while they are secured together. The layer may be secured together by stitching, crimping, quilting, drying or drying in a vacuum.

The clamp may include a slot which serves as a suturing guide. Also, the outline of the clamp may be used as a cutting guide. In addition to cutting the outline of the desired anatomical shape, the multi-layers may be sculptured in the cross-section to the desired anatomical shape.

The reconstructive structure just described may be used for reconstructing a cartilaginous element in situ. The method includes removing at least a portion, if not substantially all of the cartilaginous element, but leaving a seed portion, sculpting a reconstructive structure formed of plural layers of small intestine submucosa to the anatomical shape of the cartilaginous element being reconstructed, and positioning it adjacent to the seed portion of the cartilaginous element. The reconstructive element is secured to the seed portion of the cartilaginous element such that the reconstructive structure forms the substrate for endogenous cartilage growth from the seed portion.

A method for reconstructing a joint having two bones separated by a cartilaginous material includes removing any remaining portion of the cartilaginous material down to a bleeding bone site. A reconstructive structure formed of small intestine submucosa is positioned adjacent to the bleeding bone site and secured to the bleeding bone site so that the reconstructive structure forms a substrate for cartilaginous growth from the bleeding bone site. This provides a cartilaginous layer of material on the bone site. As an alternative, a membrane or barrier may be inserted to cover the area of the bleeding bone and the reconstructive element may be affixed to the membrane or barrier.

If a sufficient amount of cartilaginous material remains on the bone, the cartilage can be abraded to create a uniform defect without taking it to the bleeding bone. A reconstructive element is then attached to the remaining cartilaginous material.

Other objects, advantages and novel features of the present invention will become apparent from the following detailed description of the invention when considered in conjunction with the accompanying drawings.

BRIEF DESCRIPTION OF THE DRAWINGS

FIG. 4 is a perspective view of cutting the clamped plural layers using the clamp as a guide.

FIG. 5 is a perspective view of the cutting step without a guide.

FIG. 6 is a perspective view of the method of preparing the site and attaching the reconstructive structure according to the principles of the present invention.

DETAILED DESCRIPTION OF THE PREFERRED EMBODIMENTS

The starting material for the structure in accordance with the present invention comprises vertebrate submucosa, most preferably, the tunica submucosa along with a basilar portion of the tunica mucosa of a segment of intestinal tissue of a warm-blooded vertebrate. One preferred starting material comprises the tunica submucosa along with the lamina muscularis mucosa and the stratum compactum of a segment of small intestine, said layers being delaminated from both the tunica muscularis and the luminal portion of the tunica mucosa of said segment. Such a material is referred to herein as Small Intestine Submucosa ("SIS"). The thickness and definition of the basilar components of the tunica mucosa, i.e., the lamina muscularis mucosa and the stratum compactum, are known to be species dependent.

The preparation of SIS from a segment of small intestine is detailed in U.S. Pat. No. 4,902,508, the disclosure of which is expressly incorporated herein by reference. A segment of intestine, preferably harvested from porcine, ovine or bovine species, is first subject to abrasion using a longitudinal wiping motion to remove both the outer layers (particularly the tunica serosa and the tunica muscularis) and the inner layers (at least the luminal portions of the tunica mucosa). Typically, the SIS is rinsed with saline and optionally stored in a hydrated or dehydrated state until use as described below.

The method of forming a reconstructive structure for cartilaginous elements will be described specifically for a meniscus shaped cartilaginous element as an example. Specifically as discussed with respect to FIG. 6, it will be the meniscus in the knee joint.

Figure 1:
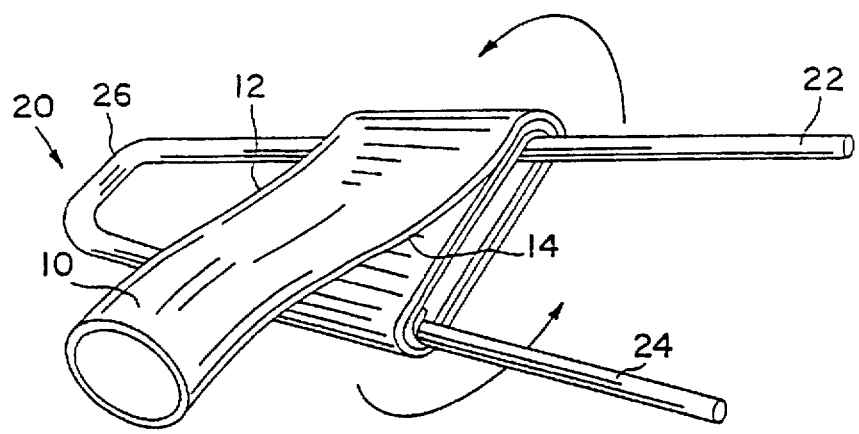
FIG. 1 is a perspective view of a mandril and method of forming a plurality of layers of small intestinal submucosa according to the principles of the present invention.

As illustrated in FIG. 1, a length of SIS 10 is wrapped around a mandril 20 having legs 22 and 24 connected at bight 26 and diverging therefrom. The SIS 10 includes two lateral edges 12 and 14 of different lengths. This is a natural condition of the material and may be considered a concave shorter or mesenteric edge 12 and a convex longer or anti-mesenteric edge 14. The diverging angle of the legs 22 and 24 of the mandril is selected to compensate for the various lengths of the edges 12 and 14 and to produce flat or planar layers. Without the mandril 20, the superimposed layers would have a tendency to buckle or the SIS would have to be stretched and thereby producing uneven tension on the surface. Once the number of layers required to duplicate the cartilaginous element to be replaced have been wrapped on the mandrel 20, the layers are compressed or clamped together for securing.

Figure 2:
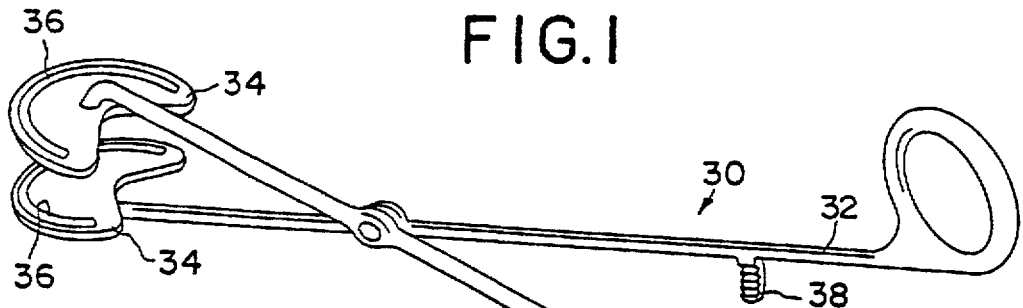
FIG. 2 is a perspective view of a clamping tool and guide according to the principles of the present invention.

Tool 30, illustrated in FIG. 2, includes a pair of arms 32 pivotally connected together and terminating in templates or clamping heads 34. The clamping heads 34 have an exterior shape of the cartilaginous element to be reconstructed. The arms 32 of the clamp 30 may include interlocking projections 38 as in other surgical or medical clamps. As previously discussed, this is a meniscus shape. Each head 34 includes a slot 36 which is a guide for suturing the layers together.

Figure 3:
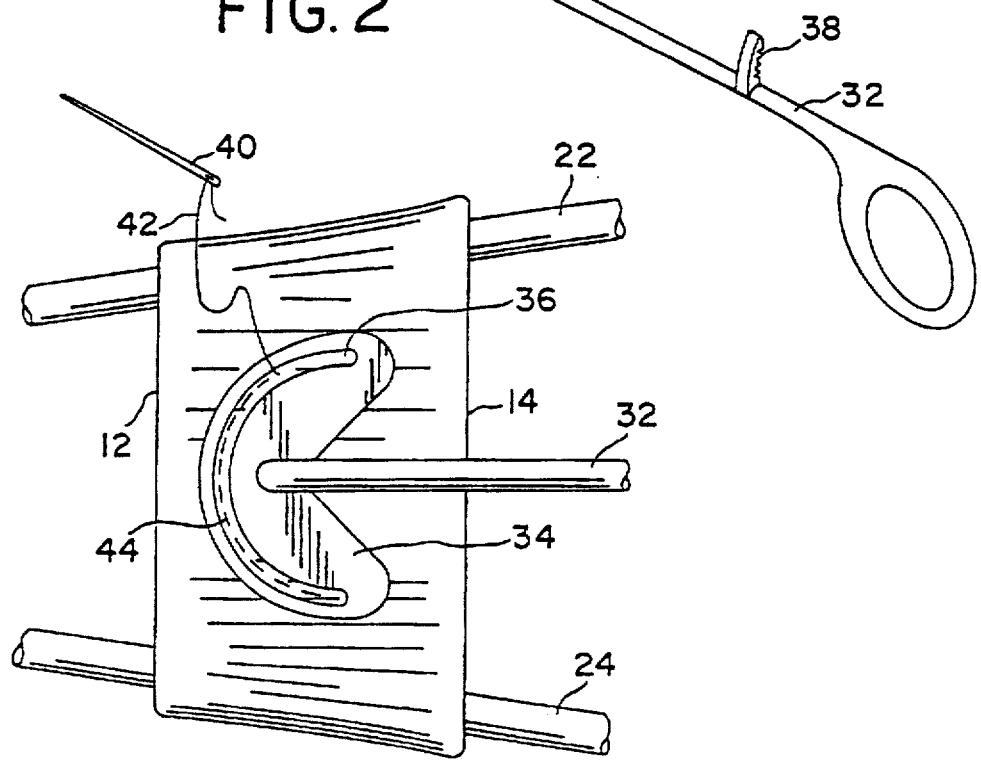
FIG. 3 is a plan view of a method of clamping and securing according to the principles of the present invention.

As illustrated in FIG. 3, the clamp 30 is applied to the plurality of the layers of SIS 10 while on the mandrel 20. One method of securing includes using a needle 40 and suture 42 to suture through the slot 36 in the template 34. Alternative methods of securing the layers together is quilting, crimping, drying and drying under a vacuum. All of these are performed while compressing the layers using the clamp 30 or other shape or style of compression plates or devices or hydraulic pressure.

The secured layers are then shaped by cutting with a knife 46 as illustrated in FIG. 4. Preferably, the clamping heads 34 form a template for the cutting as illustrated in FIG. 4. The complete meniscus shape may be cut using the heads 34 as a template or only one side thereof with the remainder being cut freehand as illustrated in FIG. 5. Alternatively, the clamp heads 34 may have a peripheral projection and used as a die in a press to cut the layers to the desired shape.

Also, since meniscus and other shapes do not have uniform cross-sections, the sculpturing of the resulting structure 16 may be performed using the knife 46. Sculpturing is intended to include the original cutting as well as cross-sectional shaping. Thus, a flat planar construct illustrated in FIG. 5 may be provided by the surgeon, who then sculptures it to replicate substantially the exact shape of the meniscus required for the appropriate patient.

Figure 11:
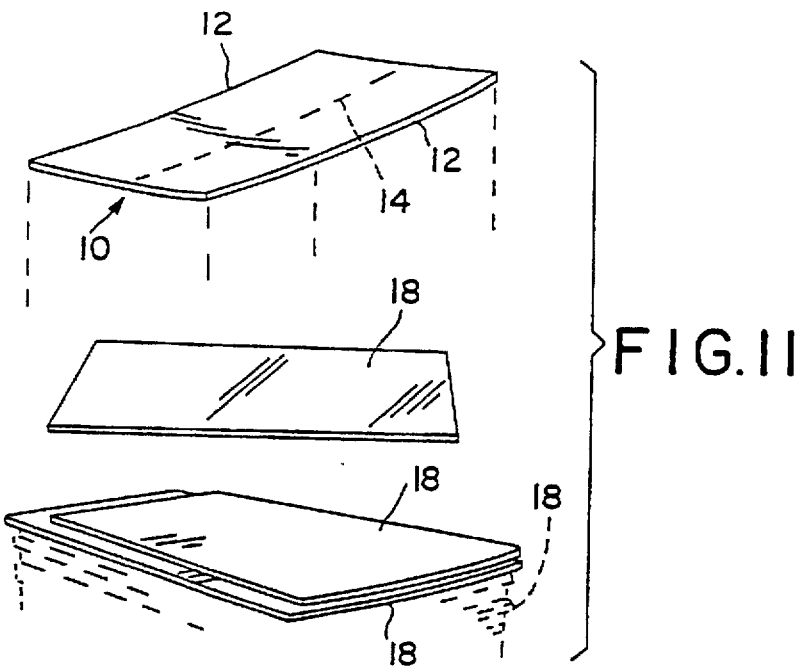
FIG. 11 is a view of a second embodiment forming a plurality of layers from sheets of small intestinal submucosa according to the principles of the present invention.

As an alternative method of forming a plurality of superimposed planar layers of SIS, the SIS 10 may be cut along its length and then cut into an appropriate size sheets. As illustrated in FIG. 11, the SIS 10 may be cut along its concave or shorter edge 12 such that the convex or longer edge 14 is in the center of the strip. This particular selection of cutting minimizes the variation in size and tension and increases the planarity. Depending upon the diameter of the SIS, it will have a width of approximately 1–2 inches. The SIS will then cut into sheets or segments 18, for example, 2–3 inches long. Other methods to form the sheets may be used.

To further remove or compensate for any variance in the individual sheets 18, the sheets may have varying angular orientation as they are stacked, as illustrated in FIG. 11.

Figure 12:
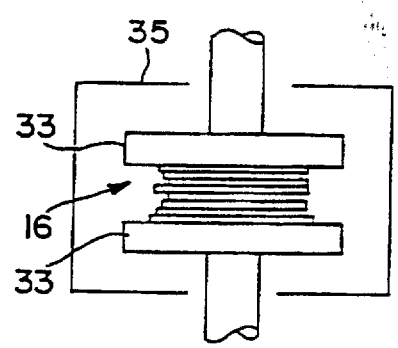
FIG. 12 is a diagrammatic view of another method of clamping and securing according to the principles of the present invention.

As an alternative to the securement of suturing of FIG. 5, the plurality of superimposed layers of SIS may be compressed between a pair of compressor plates 33 in a heating chamber 35 as illustrated in FIG. 12. This dries the compressed structure 16 and secures the plurality of layers to SIS together. The chamber 35 may be a pressurized chamber and may either increase the pressure above atmosphere or form a vacuum. A construct 16 has been formed by applying twenty pounds of pressure by the pressure plates 33 and heating at 40° C. for between 48–72 hours. Additional experiments have been conducted wherein the construct 16 is dried in a vacuum at ambient temperature, from 72 to 96 hours. The temperature may vary from ambient to 50° C. The pressure from a vacuum to 40 psi and time may vary to produce desired construct 16. The parameters are selected to prevent delamination of the plurality of layers 18 of the construct 16 while producing the desired density of the ultimate product. The number of layers may vary between 50, for example, to about 200 layers, depending upon the thickness of the individual layers, so as to produce an ultimate construct 16 having a thickness, for example, of 4–8 millimeters.

Figure 13:
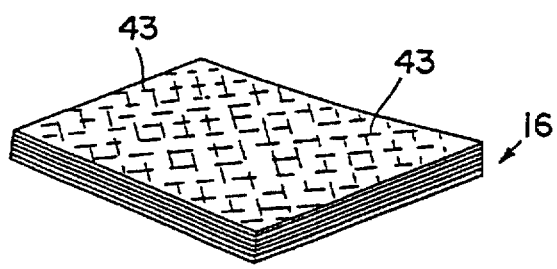
FIG. 13 is a perspective view of the method of securing using quilting according to the principles of the present invention.

As a further alternative, the plurality of layers of SIS may be secured by quilting as illustrated by the quilting pattern 43 in FIG. 13. The quilting may be produced either before, during or after drying or pressing. If performed during pressing using pressing plates, an appropriate opening must be provided in the pressing plate 33. Other methods of securing may be used. It is preferred that the securement be performed while the plurality of superimposed layers of SIS are being compressed.

As an example, the thickness of the meniscus in the knee joint may vary between four to eight millimeters in an individual, for example. Thus, a replacement reconstructive structure would include between 50 to 200 layers or more, depending upon the method of forming the structure 16. The reconstructive structure 16 of FIG. 5 is a solid multi-layer reconstructive structure having the anatomical shape of the cartilaginous element to be reconstructed. By providing the general shape of the uniform layers of SIS, sculpturing for the individual application may be achieved. Securing with suture 44 along the larger exterior radius of the structure 16 permits the securing of the elements of the unified structure and sculpturing along the other edges depending upon the structure of the bones to which the cartilaginous element is to be inserted.

The method of reconstructing a cartilaginous element in situ will be described in FIG. 6 with reference to a meniscus at the knee joint. Although the femur 50 is shown separated from the tibia 52 for sake of clearer illustration of the invention, the method includes minimum invasive surgery without the separation of the femur 50 and the tibia 52. The lateral and medial condyle of the femur 50 and the lateral and medial facet of the tibia include articular surfaces 51 and 52 respectfully of cartilaginous material. The cartilaginous material 51 and 53 are separated by medial meniscus 54 and lateral meniscus 55 which are secured by ligaments to the femur 50 and tibia 52. A portion of securing ligaments 56 and 57 for the meniscus 54 and 55 are shown.

At least the portion, if not substantially all, of a damaged cartilaginous element or meniscus 54 is removed. Preferably, a seed portion remains. If a small crescent shape is not damaged and remains, it will provide an attachment section for the reconstructive element 16 as well as a seed for the growth of the replacement cartilaginous element. Also, by leaving a crescent shape portion, the ligaments then can be used to hold the remainder of the meniscus to the bone. The replacement cartilaginous element 16 has been attached by suturing, using needle 47 and suture 48 to the remaining portion as illustrated for the lateral meniscus 55.

If the cartilaginous element or meniscus 54 is not damaged beyond repair, but only torn, small portions of the damaged cartilaginous element can be removed and replacement cartilaginous element 16 attached thereto. Alternatively, a replacement cartilaginous element 16 is sculptured to represent the damaged layers and attached directly to the in situ cartilaginous element or meniscus 54. This will strengthen the torn element without removing it. As discussed above, appropriate sculpturing is performed.

As previously discussed, the surgery is performed by minimal invasion from the side of the joint. Well known methods of cutting and suturing may be performed. If the meniscus 54 and 55 is so damaged such that a continuous crescent shape is not available for attaching, the reconstructive structure 16 may be attached to the tendon 56, 57 by any remaining seed section. The seed portion of the meniscus 54, 55 in combination with the synovial fluids support the growth of cartilaginous material using the SIS as a matrix or substrate.

The reconstructive structure of the present invention can also be used to repair, in situ, the articulation cartilage 51 and 52 on the surface of the femur 50 or tibia 52. This produces hyaline cartilage. The areas where the method is used is the tibia plateau, the femoral condyle, the femoral head and acetabula, ankle joint, elbow joint, shoulder joint, finger joints. The desired thickness of the SIS structure 16 is provided and secured to the bone by suturing or tissue adhesive, for example, fibrin glue. The damaged cartilaginous material is scraped down to a bloody surface of the bone to allow the necessary seed site for the growth of the cartilaginous material. Alternatively, a membrane or barrier may be inserted to cover the area of the bleeding bone, and the reconstructive element is affixed to that membrane or barrier. A barrier is used to separate the bleeding bone from the reconstructive element, for example, and may include ceramic or a resorbable membrane. The membrane is secured by tacking or any other method. If the cartilaginous material on the bone is not substantially damaged, the cartilage is abraded to create a uniform damaged area without taking it to the bleeding bone. The reconstructive element is then attached to the remaining cartilaginous material by suturing or using a tissue adhesive.

Figure 7:
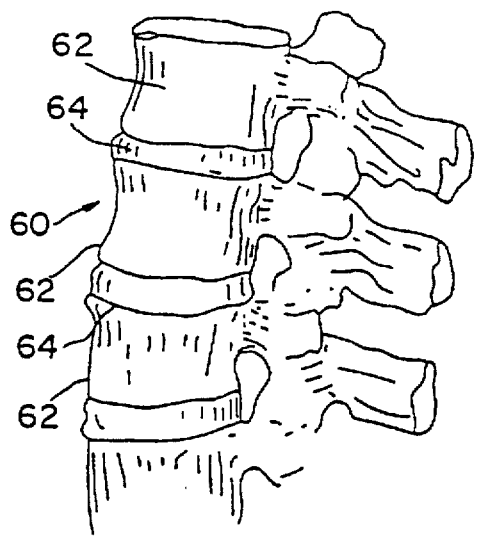
FIG. 7 is a perspective view of a backbone.

The same process may be used to replace intervertebral disc. As illustrated in FIG. 7, the vertebral body 62 is separated by intervertebral disc 64 of cartilaginous material. Reconstruction of an intervertebral disc 64 can be accomplished according to the method described with respect to FIG. 6 by attaching the SIS shaped disc to a remaining undamaged disc portion. Alternatively, fusion may take place between the adjacent vertebral body 62. The broken or split intervertebral disc 64 is removed down to a bleeding bone. The reconstructive structure of SIS formed by the method described to FIGS. 1–5 or 11–13 is inserted between the vertebral body 62. The bloody bone becomes the seed site and the SIS reconstructive structure forms a matrix for forming a bony structure. This is an example of a fibrocartilage structure. Other formations of the fibro structure would be the symphysis pubis mandibular joint and sterno clavicular joint.

Other types of cartilage or elastic cartilage is used in reconstructive surgery to model facial features such as nose and ears. The reconstructive structure formed according to the method of FIGS. 1–5 may be used for the substrate or reconstruction of elastic cartilage.

Figure 8:
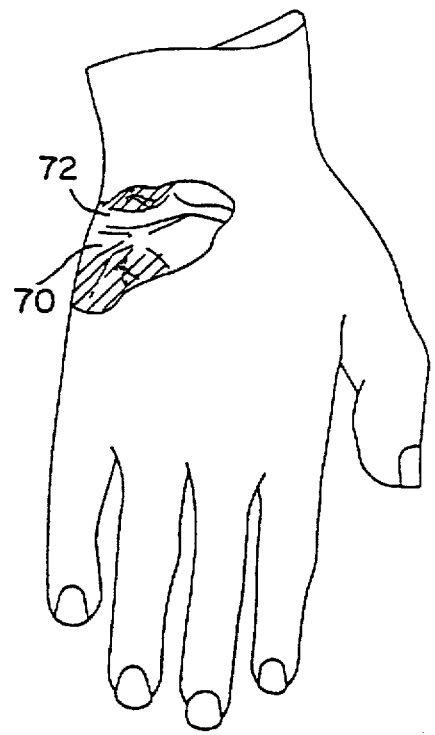
FIG. 8 is a cut-away perspective view of a wrist.
Figure 9:
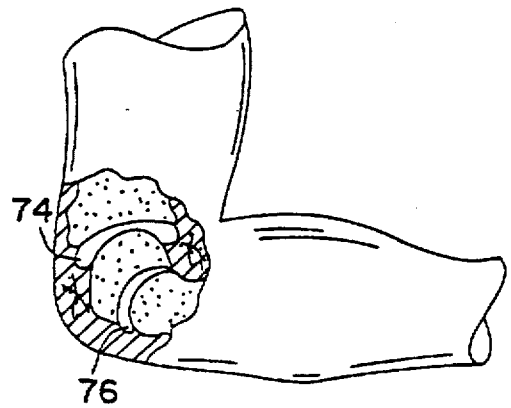
FIG. 9 is another cut-away view of a wrist.

As illustrated in FIG. 8, a cartilaginous meniscus 70 and articular disc 72 in the wrist may be restructured using the present method. Similarly, as illustrated in FIG. 9, the radiocarpal articulation 74 and the intercarpal articulation 76 in the hand may also be reconstructed using the method of the present invention.

Figure 10:
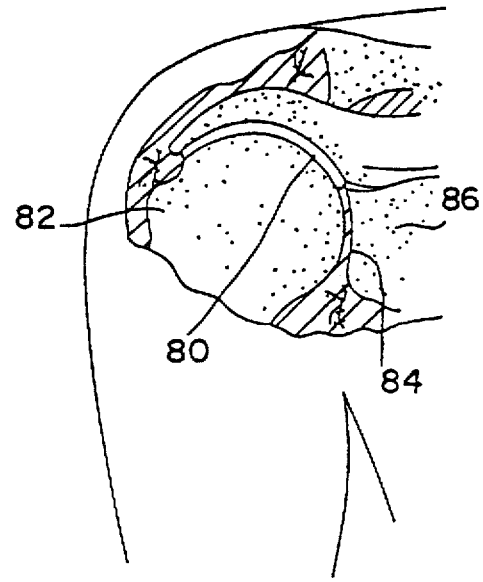
FIG. 10 is a cut-away view of a shoulder.

As illustrated in FIG. 10, the articular cartilage 80 on the humerus 82 rides on the cartilage 84 in the glenoid cavity of the scapula 86. Both the articular cartilage 82 and the cartilage of the glenoid cavity 84 may be replaced using the method of the present invention.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A method of forming a tissue graft construct for replacement or repair of a cartilaginous structure, said method comprising:

superimposing a plurality of layers of intestinal submucosa and securing the layers together by drying said layers while applying a vacuum to form a multi-layered construct having a thickness of about 4 to about 8 millimeters; and cutting the secured layers into the anatomical shape of the cartilagineous structure to be replaced or repaired.

2. A method of forming a tissue graft construct for replacement or repair of cartilaginous tissues, said method comprising:

wrapping a continuous piece of intestinal submucosa about a pair of spaced mandrels to form a multi-layered construct;

securing the layers together, and cutting the secured layers into the anatomical shape of the cartilagineous structure to be replaced or repaired.

3. The method of claim 2, wherein said intestinal submucosa is in the form of a tube having a concave and a convex lateral edge, the mandrels are positioned to diverge at an acute angle from an apex, and the tube is wrapped onto the mandrels with the concave edge closer to the apex than the convex edge.

4. The method of claim 2, wherein said graft construct comprises about 50 to about 200 layers of intestinal submucosa.

5. The method of claim 3, wherein the mandrels are wrapped with a sufficient number of layers to form a tissue graft construct having a thickness of about 4 to 8 millimeters.

6. The method of claim 3, wherein said layers are compressed while the layers are secured.

7. The method of claim 6, wherein said layers are compressed with a clamp.

8. The method of claim 7, wherein a portion of said clamp is used as a cutting guide.

9. The method of claim 7, wherein said layers are cut using said clamp as a die in a press.

10. The method of claim 3, wherein the step of securing the layers comprises drying said layers while compressing the layers.

11. The method of claim 3, wherein said layers are secured by sutures.

* * * * *